(12) United States Patent
Bronkalla et al.

(10) Patent No.: US 11,449,996 B2
(45) Date of Patent: Sep. 20, 2022

(54) INTELLIGENT AUTOMATIC SELECTION OF A PRIOR COMPARISON STUDY

(71) Applicant: INTERNATIONAL BUSINESS MACHINES CORPORATION, Armonk, NY (US)

(72) Inventors: Mark D. Bronkalla, Waukesha, WI (US); James Boritz, Toronto (CA); John Hansen, Hartland, WI (US)

(73) Assignee: MERATIVE US L.P., Ann Arbor, MI (US)

( * ) Notice: Subject to any disclaimer, the term of this patent is extended or adjusted under 35 U.S.C. 154(b) by 72 days.

(21) Appl. No.: 16/544,835

(22) Filed: Aug. 19, 2019

(65) Prior Publication Data

US 2021/0056696 A1 Feb. 25, 2021

(51) Int. Cl.
*G06K 9/00* (2022.01)
*G06T 7/00* (2017.01)
*G16H 30/20* (2018.01)

(52) U.S. Cl.
CPC ........... *G06T 7/0014* (2013.01); *G16H 30/20* (2018.01)

(58) Field of Classification Search
CPC .............................. G06T 7/0014; G16H 30/20
See application file for complete search history.

(56) References Cited

U.S. PATENT DOCUMENTS

| 5,878,223 A | 3/1999 | Becker et al. |
| 2010/0080427 A1 | 4/2010 | Yeluri et al. |
| 2016/0292155 A1 | 10/2016 | Adriaensens et al. |
| 2016/0364862 A1* | 12/2016 | Reicher .................. G16H 50/50 |
| 2018/0068066 A1 | 3/2018 | Bronkalla |
| 2018/0068072 A1 | 3/2018 | Bronkalla |
| 2018/0068079 A1 | 3/2018 | Bronkalla et al. |
| 2021/0027883 A1* | 1/2021 | Kumar ................... G16H 30/40 |

OTHER PUBLICATIONS

A. Bui, "Problem-oriented prefetching for an integrated clinical imaging workstation" Journal of the American Medical Informatics Association: JAMIA vol. 8,3 (2001): 242-53.
E. Monteiro, "Caching and prefetching images in a web-based DICOM viewer," 2016 IEEE 29th International Symposium on Computer-Based Medical Systems (CBMS), Dublin, 2016, pp. 241-246.
C. Viana-Ferreira, "An intelligent cloud storage gateway for medical imaging." (Submitted on Jul. 27, 2017) https://arxiv.org/abs/1708.06334.

* cited by examiner

*Primary Examiner* — Xin Jia
(74) *Attorney, Agent, or Firm* — Michael Best & Friedrich LLP

(57) ABSTRACT

Systems and methods for selecting a prior comparison study. One system includes an electronic processor configured to, for a medical image study associated with a patient, select a prior comparison image study. The electronic processor is also configured to automatically determine, based on monitored user interaction with the selected prior comparison image study, a usefulness of the selected prior comparison image study. The electronic processor is also configured to automatically update a selection model based on the usefulness of the prior comparison image study to a user.

17 Claims, 3 Drawing Sheets

INTELLIGENT AUTOMATIC SELECTION OF A PRIOR COMPARISON STUDY

FIELD

Embodiments described herein relate to selecting a prior comparison study, and, more particularly, to intelligent automatic selection of a prior comparison study.

SUMMARY

A picture archiving and communication system ("PACS") is a medical imaging system that provides storage and access to images from multiple modalities. In many healthcare environments, electronic images and reports are transmitted digitally via a PACS, thus eliminating the need to manually file, retrieve, or transport film jackets. A standard format for PACS image storage and transfer is digital imaging and communications in medicine ("DICOM"). Non-image data, such as scanned documents, may be incorporated using various standard formats such as portable document format ("PDF") encapsulated in DICOM.

When reading a current imaging study, the reader, often a radiologist but sometimes an orthopedic surgeon or other specialist, may obtain important context by seeing relevant prior comparison exams. For example, a wrist or an elbow would be relevant to a forearm. A chest x-ray or MR may be relevant to a shoulder image. Additionally, when reading prior comparison image studies, the reader is generally trying to answer questions related to whether a feature (for example, a fracture, tumor, cyst, or stenosis) is new, whether a feature has changed (for example, growth of a tumor, shrinkage of a tumor, healing of a fracture, or an increase in plaque, stenosis, aneurysm, effusion, or atrophy), or are there additional features (for example, metastases or stenosis).

With PACS and vendor neutral archive ("VNA") systems there is a need for a mechanism to move prior comparison imaging studies from one system (or location) to another system (or location) based on a triggering event, such as an order for a new study for an existing patient. Prior comparison imaging studies may be moved from a VNA system to a PACS system, from a PACS system to another PACS system, from a PACS system to a viewer, and the like. Conventionally, prior imaging studies to move may be selected by applying simple rules, such as based on matching a study to a modality (for example, CT, MR, or DX), a body part, a time frame (for example, most recent three years), and the like. Such rules may be used individually or in combination. Such a rules-based approach does not work well for patients having a large number of prior comparison imaging studies (for example, more than 100 and, in some cases, more than 1000). Moving such a large number of prior comparison imaging studies is infeasible. Additionally, existing prior relevancy rules are configured or hard coded into the PACS system or viewer, which makes them difficult to change or customize and resources are wasted when such rules are configured too broad or too narrow.

For example, when the relevancy rules are too narrow, the prior comparison study that is most appropriate may not be available to the reading physician. However, when the relevancy rules are set too broadly, the amount of data (the number of prior comparison studies) to be transferred may run into other bottlenecks (for example, bandwidth and processing power) that may bog down the entire system or, due to a lack of prioritization of the retrievals, hinder the availability of the most relevant study, as there are many (sometimes hundreds) of studies queued ahead of it for transfer. Wide area network ("WAN") bandwidth is generally not unlimited and notably outbound/upload capability from a given site may be substantially less than the download/inbound bandwidth available. This becomes more acute with reading physicians being more specialized and dispersed as the reading physicians are commonly reading for a variety of institutions, not just the studies that were performed at the same site that the reading physicians are reading at.

Other factors that exacerbate the problem of existing systems include the late dispatch of orders, the increasing size of studies (for example, a 70 MB 2D mammogram versus a 2-3 GB 3D mammogram), and the drive to ever thinner slices for CT scans and MR scans that is doubling the study sizes. Accordingly, for every factor that seems to offer mitigation of the problems (more bandwidth), imaging technology advances exacerbate the problems by almost exponentially increasing the amount of data to transfer.

Therefore, there is a need to for an improved selection approach to selecting studies to prefetch (for example, move to a second system or location for viewing) based on, for example, a new set of parameters, such as a patient study, history information, physician usage patterns, or a combination thereof.

To address these and other problems, embodiments described herein use patterns of selection and use of prior comparison studies by a reading physician to create new relevancy relationships. Such relevancy relationships may be used to drive one or more of prefetching, precaching, initial selection and display of a most appropriate (relevant) prior comparison study (with or without a hanging protocol), or a combination thereof.

Accordingly, embodiments described herein provide systems and methods for selecting a prior comparison study. For example, one embodiment provides a system for selecting a prior comparison image. The system includes an electronic processor configured to, for a medical image study associated with a patient, select a prior comparison image study. The electronic processor is also configured to automatically determine, based on monitored user interaction with the selected prior comparison image study, a usefulness of the selected prior comparison image study. The electronic processor is also configured to automatically update a selection model based on the usefulness of the prior comparison image study to a user.

Another embodiment provides a method of selecting a prior comparison image. The method includes, for a medical image study associated with a patient, selecting, with an electronic processor, a prior comparison image study. The method also includes automatically determining, with the electronic processor, based on monitored user interaction with the selected prior comparison image study, a usefulness of the selected prior comparison image study. The method also includes automatically updating, with the electronic processor, a selection model based on the usefulness of the prior comparison image study to a user.

Yet another embodiment provides a non-transitory computer readable medium including instructions that, when executed by an electronic processor, causes the electronic processor to execute a set of functions. The set of functions includes, for a medical image study associated with a patient, selecting a prior comparison image study. The set of functions also includes automatically determining based on monitored user interaction with the selected prior comparison image study, a usefulness of the selected prior comparison image study. The set of functions also includes automatically updating a selection model based on the usefulness of the prior comparison image study to a user.

Other aspects of the embodiments will become apparent by consideration of the detailed description and accompanying drawings.

DETAILED DESCRIPTION

Figure 1:
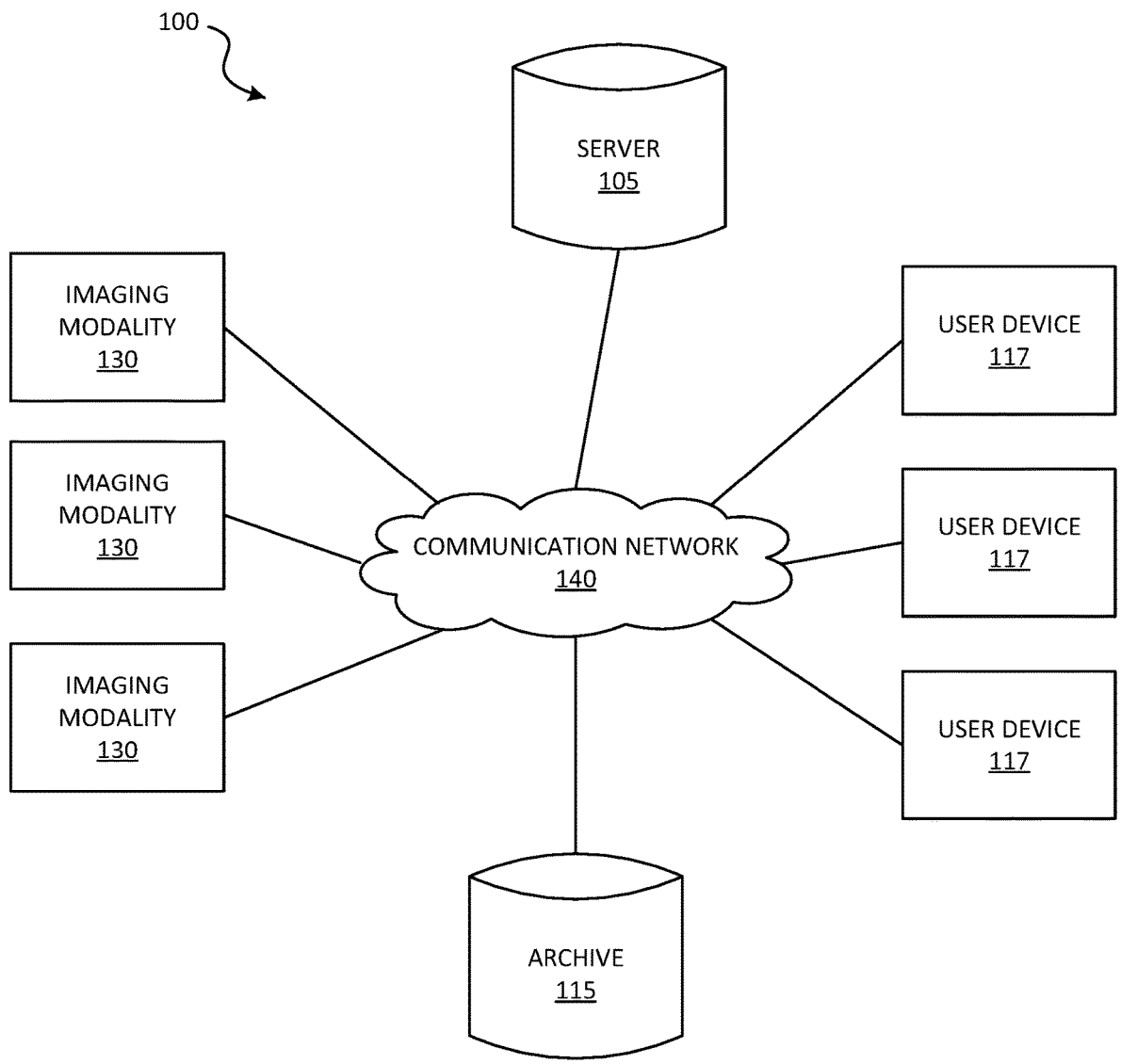
FIG. 1 illustrates a system for selecting a prior comparison study according to some embodiments.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

As discussed above, when reading a current imaging study, the reader, often a radiologist but sometimes an orthopedic surgeon or other specialist, may obtain important context by seeing relevant prior comparison exams. However, existing rules used to obtain or retrieve prior comparison imaging studies suffer from numerous deficiencies, as described above. Therefore, there is a need to for an improved selection approach to selecting studies to prefetch (for example, move to a second system or location for viewing) based on, for example, a new set of parameters, such as a patient study, history information, physician usage patterns, or a combination thereof.

To address these and other problems, embodiments described herein use patterns of selection and use of prior comparison studies by a reading physician to create new relevancy relationships. Such relevancy relationships may be used to drive one or more of prefetching, precaching, initial selection and display of a most appropriate (relevant) prior comparison study (with or without a hanging protocol), or a combination thereof.

FIG. 1 schematically illustrates a system 100 for selecting a prior comparison study (for example, a prior comparison image or set of images) according to some embodiments. The system 100 includes a server 105, an archive 115, a plurality of user devices 117 (referred to herein collectively as "the user devices 117" and individually as "the user device 117"), and a plurality of imaging modalities 130 (referred to herein collectively as "the imaging modalities 130" and individually as "the imaging modality 130"). In some embodiments, the system 100 includes fewer, additional, or different components than illustrated in FIG. 1. For example, the system 100 may include multiple servers 105, archives 115, or a combination thereof.

The server 105, the archive 115, the user devices 117, and the imaging modalities 130 communicate over one or more wired or wireless communication networks 140. Portions of the communication network 140 may be implemented using a wide area network, such as the Internet, a local area network, such as a Bluetooth™ network or Wi-Fi, and combinations or derivatives thereof. Alternatively or in addition, in some embodiments, components of the system 100 communicate directly as compared to through the communication network 140. Also, in some embodiments, the components of the system 100 communicate through one or more intermediary devices not illustrated in FIG. 1.

Figure 2:
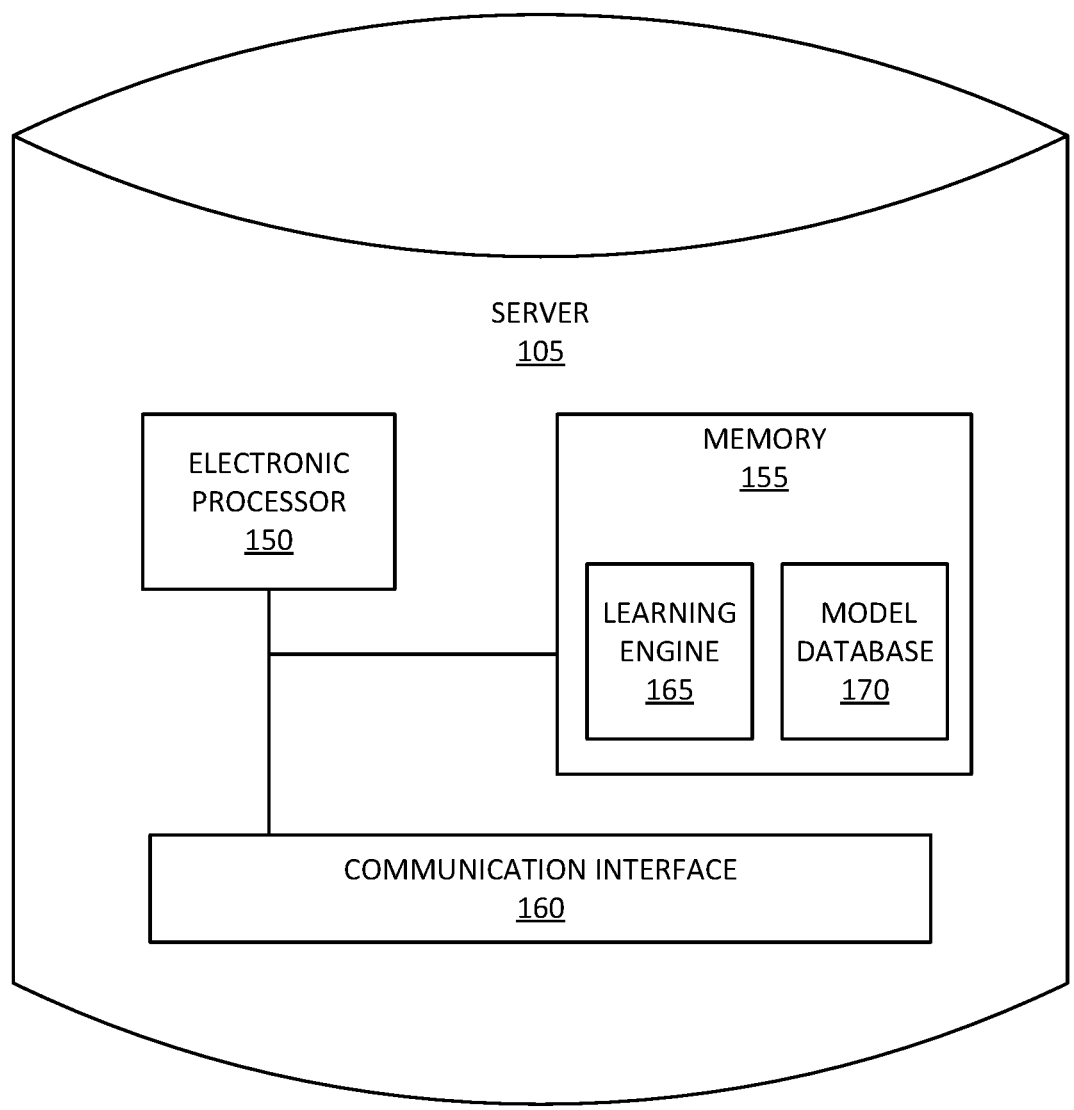
FIG. 2 illustrates a server included in the system of FIG. 1 according to some embodiments.

The server 105 is a computing device, which may serve as a gateway for the archive 115. For example, in some embodiments, the server 105 may be a PACS server. Alternatively, in some embodiments, the server 105 may be a server that communicates with a PACS server to access the archive 115. As illustrated in FIG. 2, the server 105 includes an electronic processor 150, a memory 155, and a communication interface 160. The electronic processor 150, the memory 155, and the communication interface 160 communicate wirelessly, over one or more communication lines or buses, or a combination thereof. The server 105 may include additional components than those illustrated in FIG. 2 in various configurations. The server 105 may also perform additional functionality other than the functionality described herein. Also, the functionality described herein as being performed by the server 105 may be distributed among multiple devices, such as multiple servers included in a cloud service environment. In addition, in some embodiments, the user devices 117 may be configured to perform all or a portion of the functionality described herein as being performed by the server 105.

The electronic processor 150 includes a microprocessor, an application-specific integrated circuit (ASIC), or another suitable electronic device for processing data. The memory 155 includes a non-transitory computer-readable medium, such as read-only memory ("ROM"), random access memory ("RAM") (for example, dynamic RAM ("DRAM"), synchronous DRAM ("SDRAM"), and the like), electrically erasable programmable read-only memory ("EEPROM"), flash memory, a hard disk, a secure digital ("SD") card, another suitable memory device, or a combination thereof. The electronic processor 150 is configured to access and execute computer-readable instructions ("software") stored in the memory 155. The software may include firmware, one or more applications, program data, filters, rules, one or more program modules, and other executable instructions. For example, the software may include instructions and associated data for performing a set of functions, including the methods described herein.

For example, as illustrated in FIG. 2, the memory 155 may store a learning engine 165 and a model database 170. In some embodiments, the learning engine 165 develops a model using one or more machine learning functions. Machine learning functions are generally functions that allow a computer application to learn without being explicitly programmed. In particular, a computer application performing machine learning functions (sometimes referred to as a learning engine) is configured to develop an algorithm based on training data. For example, to perform supervised learning, the training data includes example inputs and corresponding desired (for example, actual) outputs, and the learning engine progressively develops a model that maps inputs to the outputs included in the training data. Machine learning may be performed using various types of methods and mechanisms including but not limited to decision tree learning, association rule learning, artificial neural networks, inductive logic programming, support vector machines, clustering, Bayesian networks, reinforcement learning, representation learning, similarity and metric learning, sparse dictionary learning, and genetic algorithms.

Using all of these approaches, a computer program may ingest, parse, and understand data and progressively refine models for data analytics, including image analytics.

Models generated by the learning engine 165 may be stored in the model database 170. As illustrated in FIG. 2, the model database 170 is included in the memory 155 of the server 105. It should be understood that, in some embodiments, the model database 170 is included in a separate device accessible by the server 105 (included in the server 105 or external to the server 105).

The communication interface 160 allows the server 105 to communicate with devices external to the server 105. For example, as illustrated in FIG. 1, the server 105 may communicate with the archive 115, the user devices 117, the imaging modalities 130, or a combination thereof through the communication interface 160. In particular, the communication interface 160 may include a port for receiving a wired connection to an external device (for example, a universal serial bus ("USB") cable and the like), a transceiver for establishing a wireless connection to an external device (for example, over one or more communication networks 140, such as the Internet, local area network ("LAN"), a wide area network ("WAN"), and the like), or a combination thereof.

The user device 117 is also a computing device and may include a desktop computer, a terminal, a workstation, a laptop computer, a tablet computer, a smart watch or other wearable, a smart television or whiteboard, or the like. Although not illustrated, the user device 117 may include similar components as the server 105 (an electronic processor, a memory, and a communication interface). The user device 117 may also include a human-machine interface for interacting with a user. The human-machine interface may include one or more input devices, one or more output devices, or a combination thereof. Accordingly, in some embodiments, the human-machine interface allows a user to interact with (for example, provide input to and receive output from) the user device 117. For example, the human-machine interface may include a keyboard, a cursor-control device (for example, a mouse), a touch screen, a scroll ball, a mechanical button, a display device (for example, a liquid crystal display ("LCD")), a printer, a speaker, a microphone, or a combination thereof. In some embodiments, the human-machine interface includes a display device. The display device may be included in the same housing as the user device 117 or may communicate with the user device 117 over one or more wired or wireless connections. For example, in some embodiments, the display device is a touchscreen included in a laptop computer or a tablet computer. In other embodiments, the display device is a monitor, a television, or a projector coupled to a terminal, desktop computer, or the like via one or more cables. Some of these devices may have severe memory or computational capacity constraints placing an even greater emphasis on intelligent prefetching of a study or a study element.

The imaging modalities 130 provide imagery (for example, medical images). The imaging modalities 130 may include a computed tomography (CT), a magnetic resonance imaging (MRI), an ultrasound (US), another type of imaging modality, or a combination thereof. While the embodiments described herein are generally described in the context of radiology or cardiology medical images, it should be understood that other images, such as pathology images, including gross specimen photos, microscopy slide images, and whole scanned slide datasets, may also be used. Other images, such as dermatology, intra-operative or surgery, or wound care photos or movies, may also be used. In some embodiments, the medical images are transmitted from the imaging modality 130 to a PACS Gateway (for example, the server 105), before being stored in the archive 115.

The archive 115 stores a plurality of medical images (referred to herein collectively as "the medical images" and individually as "the medical image"). Accordingly, the archive 115 provides for the storage and retrieval of images and reports. In some embodiments, the archive 115 is combined with the server 105. Alternatively or in addition, the medical images may be stored within a plurality of databases, such as within a cloud service. Although not illustrated in FIG. 1, the archive 115 may include components similar to the server 105, such as an electronic processor, a memory, a communication interface and the like. For example, the archive 115 may include a communication interface configured to communicate (for example, receive data and transmit data) over the communication network 140.

A user may use the user device 117 to access and view medical images. Accordingly, in some embodiments, the user devices 117 are workstations for interpreting and reviewing medical images (for example, one or more images) stored in the archive 112. For example, a radiologist may use the user device 117 as a viewing or reading workstation to review a patient's study (a current or a new study or one or more prior comparison studies) and formulate a diagnosis for the patient. In some embodiments, a secured network is used for the transmission of patient information between the components of the system 100 (for example, the communication network 140).

For example, in some embodiments, the electronic processor 150 receives the medical image as a new medical image associated with a patient from one of the imaging modalities 130 (via the communication network 140). For example, when a new medical imaging study is ordered for a patient and captured by one of the imaging modalities 130, the new medical image is transmitted from the imaging modality 130 to the electronic processor 150. Alternatively or in addition, in some embodiments, the electronic processor 150 receives the medical image from the archive 115 in response to a request for the medical image from a user. For example, a user may use the user device 117 to initiate a request for a particular medical image associated with a patient. In response to receiving the request for the particular medical image, the electronic processor 150 receives the medical image from the archive 115. Accordingly, in some embodiments, the medical image received by the electronic processor 150 is a prior comparison image and is included in the plurality of prior comparison images stored in the archive 115.

In some embodiments, the user devices 117 are web-based viewers. For example, the user may access the medical images from the archive 115 (through a browser application or a dedicated application stored on the user device 117 that communicates with the server 105) and view the medical images on the display device associated with the user device 117. Accordingly, in some embodiments, the user devices 117 provide web-based interfaces. Such web-based interfaces may be accessed via the Internet or a wide area network ("WAN"). In some embodiments, connection security is provided by a virtual private network ("VPN"), a secure sockets layer ("SSL"), or a combination thereof. A client's side software (at a user device 117) may comprise ActiveX, JavaScript, a Java Applet, or an iOS or Android application. PACS clients may also be full applications, which utilize the full resources of the computer that the PACS clients are executing on outside of a web environment.

As noted above, the quantity of available prior comparison studies for a given patient and the limitations associated with existing rule-based selection approaches interfere with a reviewer's ability to efficiently access and view prior comparison studies associated with a patient, and, ultimately, with the reviewer's ability to formulate a diagnosis for the patient. To solve this and other problems, the system 100 is configured to automatically select (prefetch) prior comparison studies (for example, a first medical image, a second medical image, and the like). Based on the selection of the prior comparison studies, the methods and systems described herein display the selected prior comparison studies to a user (for example, a reviewer).

Figure 3:
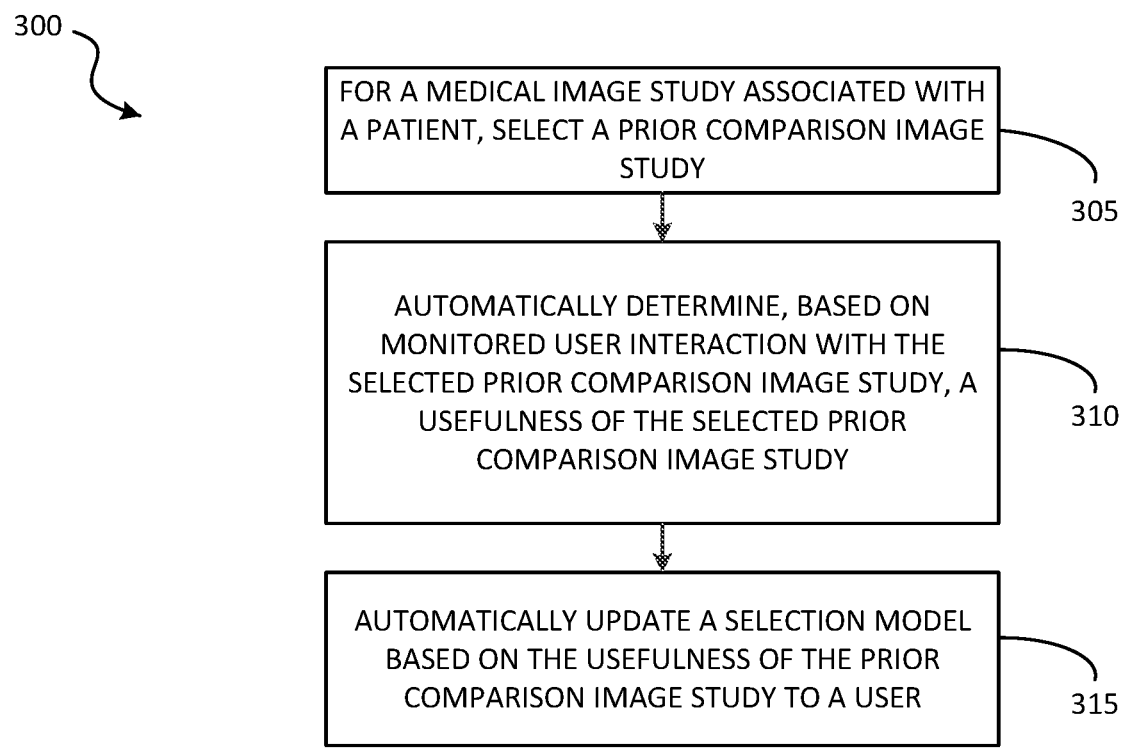
FIG. 3 is a flowchart illustrating a method for selecting a prior comparison study using the system of FIG. 1 according to some embodiments.

For example, FIG. 3 is a flowchart illustrating a method 300 for selecting a prior comparison study (for example, a medical image or set of images) according to some embodiments. The method 300 is described here as being performed by the server 105 (the electronic processor 150 executing instructions). However, as noted above, the functionality performed by the server 105 (or a portion thereof) may be performed by other devices, including, for example, the user device 117 (via an electronic processor executing instructions).

As illustrated in FIG. 3, the method 300 includes, for a medical image study associated with a patient, selecting, with the electronic processor 150, a prior comparison image study (at block 305). In some embodiments, the electronic processor 150 automatically selects the prior comparison image study using a selection model. Alternatively or in addition, in some embodiments, the electronic processor 150 automatically selects the prior comparison image study based on one or more selection rules. The selection rule may be a predetermined (preset) selection rule or a dynamic selection rule that is modified based on monitored user interactions, extracted attributes, or a combination thereof (as described in greater detail below). Similarly, as also described below, the selection model may be updated with feedback. As described below, in some embodiments, the electronic processor 150 may initially use one or more selection rules to select prior comparison image studies but may disable the one or more of the selection rules and use the selection model to automatically select the prior comparison image study as the selection model is trained using feedback on the image studies selected via the rules, the model, or both. The selection model may be built using various factors, including the factors described below. For example, training information may be obtained for historically-selected prior comparison image studies and used to generate the selection model using one or more machine learning techniques (e.g., via the learning engine 165). Accordingly, the factors discussed below may be used as part of training a selection model, as part of establishing a selection rule, or both.

As noted above, when reading a current imaging study, the reader may obtain important context by seeing relevant prior comparison exams. Accordingly, the selected prior comparison image study may include one or more prior comparison images that may be relevant to, for example, obtaining a context associated with the medical image study, the patient associated with the medical image, or a combination thereof. In other words, the selected prior comparison image study may help a reader answer questions related to whether a feature is new, whether a feature has changed, or whether there are additional features. The electronic processor 150 may automatically select the prior comparison image study as part of performing pre-fetching, pre-caching, or selecting an image study for initial display. Accordingly, in some embodiments, the electronic processor 150 transmits the prior comparison image study to a user for display via a display device of the user device 117.

In some embodiments, the electronic processor 150 selects a prior comparison image study by analyzing the medical image associated with the patient to extract one or more attributes from the medical image. The electronic processor 150 may select the prior comparison image study based on the one or more attributes extracted from the medical image. Alternatively or in addition, the electronic processor 150 selects a prior comparison image study by analyzing a medical image associated with a patient to extract one or more attributes from the medical image (a first set of attributes), analyzing a prior comparison image study to extract one or more attributes associated with the prior comparison image (a second set of attributes), and comparing the one or more attributes extracted from the medical image with the one or more attributes associated with the prior comparison image study (for example, performing a comparison of a first set of attributes with a second set of attributes). The electronic processor 150 may select a prior comparison image study based on the comparison. Alternatively or in addition, the electronic processor 150 selects a prior comparison image study by analyzing a plurality of prior comparison image studies to extract one or more attributes associated with each prior comparison image. The electronic processor 150 may then select a prior comparison image study based on the one or more attributes associated with each prior comparison image.

In some embodiments, the one or more attributes extracted from a current medical image or one or more of the plurality of prior comparison image studies may be extracted by the electronic processor 150 using natural language processing. Alternatively or in addition, the electronic processor 150 extracts the one or more attributes using ontological mapping of clinical terms or findings within an order, a report visit note, or another document associated with the medical image.

There are a number of features (or attributes) of a current medical image and a prior comparison image study that may be used in determining a usefulness (relevancy). A source of the extracted attributes may include the imaging study metadata (for example, a DICOM header). The metadata may include a variety of text (for example, a study description, a reason for exam, a body part examined, a laterality, and the like), codified data (for example, ICD 9/10 codes), a body part, a view descriptor (for example, CC ML, MLO, and other views of a breast), use of a contrast agent, a method of administration, a series description, an acquisition parameter (for example, a spin, an echo time, a relaxation time, a flip angle in an MR study) and the like. Additionally, a delta of a date of a prior comparison study and a current study may also be computed (for example, via the electronic processor 150).

Another source of the extracted attributes may include a Health-Level 7 ("HL7") Order. HL7 refers to a set of international standards for transfer of clinical and administrative data between software applications used by various healthcare provides. A HL7 Order is linked to a medical image (a medical image study) that may be extracted from the HL7 ORM (Order Message), which contains additional information that is not transferred to the image metadata. The additional information extracted from the HL7 ORM may include, for example, items such as a CPT code, a reason for an exam (much larger than may be accommodated in a DICOM header), a procedure step, and patient history questionnaire data that may have been gathered by a technologist performing the exam.

Yet another source of the extracted attributes may include a physician's report for a prior comparison image study. A physician's report may be processed using natural language processing to extract key attributes, such as a history, an indication, a finding, an impression, a conclusion, and the like. One or more of the extracted attributes may be mapped to an ontology, such as UMLS, as is done in Watson Health Imaging Patient Synopsis and Clinical Review to then allow for subsequent comparison based on standardized terminology.

A further source of the extracted attributes may include a most recent visit or clinical note for a patient by an ordering physician. The most recent visit or clinical note may be processed (with the electronic processor 150) using natural language processing to extract the one or more attributes from the clinical content of the most recent visit or clinical note. The most recent visit or clinical notes may contain more clinical context than a notoriously vague order (for example, pneumonia suspected based on patient cough and presentation, but simply order a "2 view chest x-ray" with no further information in the order).

After selecting the prior comparison image study (and transmitting the selected prior comparison image study to a user for display via a display device of the user device 117), the electronic processor 150 determines a usefulness of the prior comparison image study (at block 310). In some embodiments, the electronic processor 150 automatically determines the usefulness of the selected prior comparison image study. For example, in some embodiments, the electronic processor 150 automatically determines the usefulness of the selected prior comparison image study based on monitored user interaction with the selected prior comparison image study (considered alone or in combination with other factors, such as attributes of the selected image studies, reports associated with the selected images studies, or the like as described below).

As noted above, the electronic processor 150 may determine the usefulness of the selected prior comparison image study based on monitored user interactions with the selected prior comparison image study. The monitored user interactions may include, for example, one or more interactions of the user with the medical image, one or more prior comparison images, or a combination thereof. In particular, the monitored user interactions may include, for example, (a) a measurement of how long a prior comparison study is kept opened, (b) a last comparison study viewed (presumably answering a clinical question), (c) a first comparison opened with no additional selection (and no similar types of comparisons available), (d) a first comparison study opened (for example, many mammograph readers prefer to view the two or three year old prior comparison study presented first for comparison before reviewing some or all of the prior comparison studies), (e) text analytics finding a simple mention in a report of a prior comparison study (some PACS will note ANY study opened for comparison in the report automatically whether it was useful or not), (f) text analytics of a report of changes of an anatomical structure, a disease, a structural defect or neoplasm (tumor) where these may be qualitative of quantitative comparisons, (g) opening and discarded prior comparison images may still be valuable, but discarded or replaced comparisons may be ranked lower than a last or report mentioned prior comparison study, (h) retrievals to the PACS from the VNA (this may be confounded by automated precaching when used for one or more types of studies), (i) retrievals to the PACS of a prior comparison study that is separated in time from the rest of the prior comparison study retrievals (differentiate between automated precaching and manual selection), (j) explicit manual selection of a prior comparison study or series, and the like.

Accordingly, in some embodiments, the electronic processor 150 automatically determines the usefulness of the selected prior comparison image study by considering how long the prior comparison image study is opened, whether the prior comparison image study was the last study viewed before completing a report for the medical image study associated with the patient, or a combination thereof. Alternatively or in addition, the electronic processor 150 may automatically determine the usefulness of the selected prior comparison image study by determining whether the prior comparison image study was a first image study opened by the user, determining whether, using natural language processing of a report generated for the medical image study associated with the patient, references the prior comparison image study, or a combination thereof. Alternatively or in addition, the electronic processor 150 may automatically determine the usefulness of the selected prior comparison image study by identifying whether another prior comparison image study was retrieved for the medical image study associated with the patient, comparing the prior comparison image study with another prior comparison image study retrieved for the medical image study associated with the patient, or a combination thereof. In some embodiments, the electronic processor 150 automatically determines a usefulness of the selected prior comparison image by determining whether, using natural language processing of a report generated for the medical image study associated with the patient, references the prior comparison image study. In some embodiments, electronic processor 150 automatically determines the usefulness of the selected prior comparison image by performing natural language processing of a report generated for the medical image study associated with the patient.

Returning to FIG. 3, the method 300 also includes updating, with the electronic processor 150, a selection model (at block 315). In some embodiments, the selection model is generated using machine learning based on historical patterns of selection and use of prior comparison studies for a plurality of medical image studies. In some embodiments, the electronic processor 150 updates the selection model automatically. In some embodiments, the electronic processor 150 updates the selection model based on the usefulness of the prior comparison image study to a user.

In some embodiments, the electronic processor 150 selects the prior comparison image study based on a previously-determined usefulness of the prior comparison image study. For example, the electronic processor 150 may select a particular prior comparison image study from a plurality of prior comparison image studies based on the usefulness of that particular prior comparison image study exceeding (or satisfying) a predetermined usefulness threshold. Alternatively or in addition, the predetermined usefulness threshold may define a total number of prior comparison images to include in the prior comparison image study. For example, when the predetermined usefulness threshold is five, the electronic processor 150 identifies the five prior comparison images having the greatest usefulness for inclusion in the selected prior comparison image study.

In some embodiments, the electronic processor 150 also determines a relevancy order for displaying each prior comparison image included in the selected prior comparison image study. The relevancy order may be based on the usefulness of each prior comparison image included in the selected prior comparison image study. In other words, the relevancy order may reflect the usefulness associated with each prior comparison image included in the selected prior comparison image study. For example, a first prior comparison image included in the selected prior comparison image study having the greatest usefulness may be in a first position of the relevancy order while a second prior comparison image included in the selected prior comparison image study having a lower usefulness than the first prior comparison image may be in a second position of the relevancy order (the next position of the relevancy order after the first position). Accordingly, the usefulness may be used not just to drive prefetching or precaching of prior comparison studies, but also a display order of the prior comparisons within a PACS viewer, replacing the traditional hanging protocol prior relevancy rules or selection process, such that the most appropriate prior comparison study is loaded automatically and the next most relevant prior comparison studies are either available for manual selection, concurrent display, or sequential display.

In some embodiments, the monitored user interactions may include a request for an additional prior comparison image. For example, the electronic processor 150 may receive a request for an additional prior comparison image from the user. In response to receiving the request for the additional prior comparison image, the electronic processor 150 may transmit the additional prior comparison image to the user for display. In some embodiments, the electronic processor 150 uses the request for an additional prior comparison image from the user as feedback (training data) for selecting prior comparison images (using the selection model developed with machine learning). In particular, the electronic processor 150 may update the selection model based on the request for the additional prior comparison image. In some embodiments, the electronic processor 150 automatically selects a new prior comparison image study using the updated selection model and transmits the new prior comparison image study to a user for display.

Accordingly, with the "extracted attribute sets" available for the current medical image, one or more prior comparison images, or a combination thereof, the system 100 may not only be preconfigured or trained to provide an appropriate set of prior relevancy criteria (for example, the selected prior comparison image study) based on the broad set of extracted attributes from the sources mentioned above, but also learn from the actions (monitored user interactions) of the reading physician either individually/personally or in aggregate (for example, to update the selection model). Alternatively or in addition, in some embodiments, the electronic processor 150 uses one or more selection rules as a means to prime the selection process until intelligent selection is trained.

With the extracted attributes available for comparison and determining usefulness (relevancy), the system 100 is able to learn better associations (between a current medical image and one or more prior comparison studies) that may be applied by simple rules (selection rules or modified selection rules based on monitored user interactions). As noted above, user actions may be monitored as well as natural language processing extraction from a current medical image and related documents (for example, an order, a visit note, a report, and the like) to then provide the system 100 the ability to learn prior relevancy patterns (monitored user interactions) and update the prior relevancy patterns in a continuous learning process. In some embodiments, usage patterns and resulting imaging report content may replace a process of manually annotating training data sets with a continuous feedback process that may either be purely implicit with no overt user actions in training the system 100 (for example, one or more models) or explicit where a user may indicate that a suggested prior comparison image has either high or low relevancy (usefulness) and why. In other words, by applying the monitored user interactions, extracted attributes, or a combination thereof described herein along with a user indication of a closeness of match or best prior relevancy as a corrective or annotative input to the learning process, where the extracted feature sets (attributes) may be the original data input into the learning process, the system 100 (for example, one or more models) may be trained to better select prior comparison studies and rank the prior comparison studies in an order in which the prior comparison studies may be retrieved.

Embodiments described herein may be either deeply integrated into a PACS viewer or alternatively used on a VNA or PACS server (for example, the server 105), where all that may be seen are the retrievals by a viewer or PACS client. When applying the embodiments described herein to existing PACS or VNA, not all of the feature set information may be available (for example, no visit or clinical notes available in an HL7 feed to the PACS). Additionally, there may only be the automated inferential feedback mechanisms (especially when dealing with third party PACS or viewers) and this is deployed as a feature of the VNA. Accordingly, in some embodiments, the methods and systems described herein provide a means of discriminating between retrievals that are driven by existing hanging protocols and relevancy rules in a viewer versus what was actually found to be most useful or relevant by a user.

Some PACS or viewers automatically retrieve a few of the most relevant prior comparison images as a background process in advance of a user opening a study for viewing. This is often referred to as "precaching" of the study. However, not all prior comparison studies or images selected for viewing will be good or optimal choices, whether this is done algorithmically with a hanging protocol or relevancy rules or done manually by a user opening a study or selecting images from the study for comparison. Therefore, a simple "was a comparison study viewed?" tracking is insufficient.

Thus, the embodiments herein provide, among other things, methods and systems that utilize actions of a user (whether directly or indirectly) to provide better prior relevancy ranking for prior comparison studies. For example, knowing which prior comparison studies were recalled or displayed, the sequencing of the prior comparison studies, a dwell or viewing time, as well as whether or not an already displayed prior comparison study was replaced, may be utilized along with metadata of a study to train the systems described herein. The metadata may come from the DICOM images of a current medical image, a prior comparison image, a HL7 order, a report associated with a prior comparison study, another type of metadata, or a combination thereof. Accordingly, the embodiments described herein prefetch and display the most relevant prior comparison studies as well as prioritize a transfer or retrieval of the next most relevant prior comparison studies.

Therefore, the embodiments herein provide, among other things, automated learning of a relevancy of prior comparison study based on user actions, such as an order and a timing of viewing of prior comparison studies and their reports, analyzed against metadata for an imaging study, an order, and a report for the prior comparison studies. User actions where prior comparison studies replace existing prior comparison studies in a PACS or another viewer and a sequence of replacement drives new learning of a prioritization ranking increase or decrease of the prior comparison study.

Various features and advantages of the invention are set forth in the following claims.

What is claimed is:

1. A system for prefetching or precaching a prior comparison image, the system comprising:
an electronic processor configured to,
in response to receiving a new medical image study for an existing patient:
automatically determine a usefulness of a prior comparison image study to the new medical image study by considering whether the prior comparison image study was a last medical mage study viewed before completing a prior report associated with the existing patient, and
automatically prefetch or precache the prior comparison image study based on the determined usefulness of the prior comparison image study to the new medical image study being above a threshold.

2. The system of claim 1, wherein the electronic processor is configured to automatically select the prior comparison image study based on a selection rule.

3. The system of claim 2, wherein the electronic processor is configured to disable the selection rule and automatically select the prior comparison image study using the selection model.

4. The system of claim 1, wherein the electronic processor is configured to automatically select the prior comparison image study using a selection model based on the usefulness of the prior comparison image study to the new medical image study.

5. The system of claim 1, wherein the electronic processor is configured to automatically determine the usefulness of the prior comparison image study to the new medical image study by considering how long the prior comparison image study was opened.

6. The system of claim 1, wherein the electronic processor is configured to automatically determine the usefulness of the prior comparison image study to the new medical image study by determining whether the prior comparison image study was a first image study opened by the user.

7. The system of claim 1, wherein the electronic processor is configured to automatically determine the usefulness of the prior comparison image study to the new medical image study by determining whether, using natural language processing of the prior report associated with the existing patient, references the prior comparison image study.

8. The system of claim 1, wherein the electronic processor is configured to automatically determine the usefulness of the prior comparison image study to the new medical image study by performing natural language processing of the prior report associated with the existing patient.

9. The system of claim 1, wherein the electronic processor is configured to automatically determine the usefulness of the prior comparison image study to the new medical image study by identifying whether another prior comparison image study was retrieved for the prior report associated with the existing patient.

10. The system of claim 9, wherein the electronic processor is configured to automatically determine the usefulness of the prior comparison image study to the new medical image study by comparing the prior comparison image study with another prior comparison image study retrieved for the prior report associated with the existing patient.

11. A method for prefetching or precaching a prior comparison image, the method comprising:
in response to receiving a new medical image study for an existing patient:
automatically determining, with an electronic processor, a usefulness of a prior comparison image study to the new medical image study by considering whether the prior comparison image study was a last study viewed before completing a prior report associated with the existing patient; and
automatically prefetching or precaching the prior comparison image study based on the determined usefulness of the prior comparison image study to the new medical image study being above a threshold.

12. The method of claim 11, further comprising automatically updating a selection model generated using machine learning based on historical patterns of selection and use of prior comparison studies for a plurality of medical image studies.

13. The method of claim 11, further comprising automatically selecting the prior comparison image study based on a selection rule.

14. The method of claim 11, further comprising automatically selecting the prior comparison image study using a selection model.

15. A non-transitory computer readable medium including instructions that, when executed by an electronic processor, causes the electronic processor to execute a set of functions, the set of functions comprising:
- in response to receiving a new medical image study for an existing patient:
  - automatically determining, with an electronic processor, a usefulness of a prior comparison image study to the new medical image study by considering whether the prior comparison image study was a last study viewed before completing a prior report associated with the existing patient; and
  - automatically prefetching or precaching the prior comparison image study based on the determined usefulness of the prior comparison image study to the new medical image study being above a threshold.

16. The non-transitory computer readable medium of claim 15, wherein the automatically determining the usefulness of the prior comparison image study to the new medical image study includes automatically determining the usefulness of the prior comparison image study to the new medical image study by determining whether the prior comparison image study was a first image study opened by a user.

17. The non-transitory computer readable medium of claim 15, wherein the set of functions further includes automatically selecting the prior comparison image study using a selection model.

\* \* \* \* \*